US012691176B2

(12) United States Patent
Selner

(10) Patent No.: US 12,691,176 B2
(45) Date of Patent: Jul. 28, 2026

(54) IONIC NANOVESICLE SUSPENSION AND BIOCIDE PREPARED THEREFROM

(71) Applicant: Marc Selner, Studio City, CA (US)

(72) Inventor: Marc Selner, Studio City, CA (US)

( * ) Notice: Subject to any disclaimer, the term of this patent is extended or adjusted under 35 U.S.C. 154(b) by 1959 days.

(21) Appl. No.: 15/549,111

(22) PCT Filed: Feb. 4, 2016

(86) PCT No.: PCT/US2016/016629
§ 371 (c)(1),
(2) Date: Aug. 4, 2017

(87) PCT Pub. No.: WO2016/126982
PCT Pub. Date: Aug. 11, 2016

(65) Prior Publication Data

US 2018/0036236 A1 Feb. 8, 2018

Related U.S. Application Data

(60) Provisional application No. 62/125,926, filed on Feb. 5, 2015.

(51) Int. Cl.

| | |
|---|---|
| ***A61K 47/06*** | (2006.01) |
| ***A61K 9/00*** | (2006.01) |
| ***A61K 9/06*** | (2006.01) |
| ***A61K 9/10*** | (2006.01) |
| ***A61K 31/14*** | (2006.01) |
| ***A61K 31/155*** | (2006.01) |
| ***A61K 31/7036*** | (2006.01) |
| ***A61K 38/12*** | (2006.01) |

(52) U.S. Cl.
CPC ............ *A61K 47/06* (2013.01); *A61K 9/0014* (2013.01); *A61K 9/06* (2013.01); *A61K 9/10* (2013.01); *A61K 31/14* (2013.01); *A61K 31/155* (2013.01); *A61K 31/7036* (2013.01); *A61K 38/12* (2013.01)

(58) Field of Classification Search
CPC .. A61K 31/14; A61K 31/155; A61K 31/7036; A61K 38/12; A61K 9/10; A61K 9/06
See application file for complete search history.

(56) References Cited

U.S. PATENT DOCUMENTS

| | | | | |
|---|---|---|---|---|
| 2002/0146440 A1* | 10/2002 | Smith | ...................... | A61K 8/67 424/401 |
| 2006/0051385 A1* | 3/2006 | Scholz | .................. | A61K 31/14 424/405 |
| 2016/0367504 A1* | 12/2016 | Burnam | .................. | A61K 9/10 |

* cited by examiner

*Primary Examiner* — Kortney L. Klinkel
(74) *Attorney, Agent, or Firm* — Handal & Morofsky LLC

(57) ABSTRACT

A stable suspension, containing water, petrolatum, and at least one ionic biocide compound, wherein the suspension contains no added emulsifier, and all ionic biocide compounds present are either all cationic or all anionic, an ointment containing the stable suspension, and a method for producing the stable suspension.

13 Claims, No Drawings

IONIC NANOVESICLE SUSPENSION AND BIOCIDE PREPARED THEREFROM

CROSS-REFERENCE TO RELATED APPLICATIONS

The present application claims priority to U.S. Provisional application Ser. No. 62/125,926, filed Feb. 5, 2015, the entire contents of which are hereby incorporated by reference.

BACKGROUND OF THE INVENTION

Field of the Invention

The present invention relates to a suspension prepared without emulsifiers, and a biocide prepared using that suspension.

Description of the Related Art

The preparation of emulsions and suspensions typically requires the use of one or more emulsifiers or other agents that serve to maintain the oil phase separated within the aqueous phase, or the aqueous phase separated within the oil phase. A problem that is often encountered is the separation of the oil and aqueous phases over time, either by coalescing of the dispersed phase, or in some cases, by the combination of dispersed phase portions in a process of flocculation (formation of solid materials within the dispersion/suspension/emulsion that results in separation of the phases, with one in solid or semi-solid form).

Accordingly, a method for creating a suspension without the use of emulsifiers that results in stable suspension that does not undergo separation of phases over suspended periods of time, and the use of such suspensions in the generation of a biocidal composition having a long-lasting high biocidal activity across a spectrum of microorganisms.

SUMMARY OF THE INVENTION

Accordingly, one object of the present invention is the preparation of a stable suspension without the use of conventional emulsifiers, by the use of ionic nanovesicles that remain in suspension without separating, coalescing or flocculating, due to ionic repulsion forces between nanovesicles within the suspension.

A further object of the present invention is the preparation of such stable suspensions of water and petrolatum, to thus provide an ointment suspension.

A still further object of the present invention is the preparation of a biocide suspension, comprising the stable suspension of the present invention in which the ionic component comprises one or more biocidal compounds.

These and other objects of the present invention have been satisfied by the discovery of a stable suspension, comprising water, petrolatum, and at least one ionic biocide compound, wherein the suspension contains no added emulsifier, and all ionic biocide compounds present are either all cationic or all anionic, wherein the at least one ionic biocide is contained within nanovesicles having a diameter of 100 microns or less, an ointment containing the stable suspension and a method for its production.

DETAILED DESCRIPTION OF THE PREFERRED EMBODIMENTS

The present invention relates to a stable suspension formed without the use of conventional emulsifiers, in which the suspension comprises water, petrolatum, and at least one ionic biocide compound. One key to making the stable suspension of the present invention is the formation of the at least one ionic biocide compound into ionic nanovesicles, through the use of heat and high shear of the entire mixture.

In one embodiment of the present invention, the stable suspension is prepared by combining an ionic biocide, water, and petrolatum as a mixture, then heating the mixture above the melting point of petrolatum. The heated mixture is subjected to high shear to result in the formation of nanovesicles containing the ionic biocide. These nanovesicles are typically 100 microns or less in diameter, more preferably 50 microns or less. Due to the heat and the ionic charge, these nanovesicles remain separate and do not join or coalesce, due to ionic repulsion forces between neighboring nanovesicles. By remaining separated and less than 100 microns, the nanovesicles thus maintain their separation, and remain in a suspended state without separating, coalescing or flocculating. Tests to separate even a drop are unsuccessful with extreme heat, cold, centrifuge, agitation, and even solvents.

The ionic biocide of the present invention can be either an anionic or cationic biocide. It is also acceptable to use a combination of one or more biocides, so long as in the case of a mixture of biocide components, all biocide components in the suspension are either anionic or cationic. This ensures that the nanovesicles formed are all of the same ionic charge, to enable them to repel one another once suspended. Preferably biocides are not mixed before forming the suspension, and, in the example of two biocides, are formed into two separate suspensions which are then combined with one another.

It is also acceptable to combine a nonionic biocide with the ionic biocide, particularly in cases where the nonionic biocide provides biocidal activity complementary to, or in addition to, the ionic biocide being used.

Examples of suitable ionic biocide compounds include, but are not limited to, Polyhexanide (polyhexamethylene biguanide, PHMB), Polyaminopropyl biguanide (PAPB), Benzalkonium chloride, Stearalkonium chloride, sodium hypochlorite (or common household bleach) and Ethylenediaminetetraacetic acid (EDTA). Preferably, the biocide is PHMB or benzalkonium chloride, and in a more preferred embodiment is a combination of PHMB and benzalkonium chloride.

Polyhexanide (polyhexamethylene biguanide, PHMB) is a polymer used as a disinfectant and antiseptic. In dermatological use, it is spelled polyhexanide (INN) and sold under names such as Lavasept, Serasept, and Omnicide. PHMB has been shown to be effective against *Pseudomonas aeruginosa, Staphylococcus aureus* (also the methicillin-resistant type, MRSA), *Escherichia coli, Candida albicans* (yeast), *Aspergillus brasiliensis* (mold), vancomycin-resistant enterococci, and *Klebsiella pneumoniae* (carbapenem-resistant enterobacteriaceae).

The chemical structure of polyhexanide is as below:

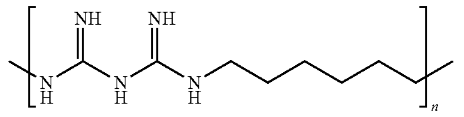

Some products containing PHMB are used for inter-operative irrigation, pre- and post-surgery skin and mucous membrane disinfection, post-operative dressings, surgical and non-surgical wound dressings, surgical bath/hydrotherapy, chronic wounds like diabetic foot ulcer and burn wound management, routine antisepsis during minor incisions, catheterization, scopy, first aid, surface disinfection, and linen disinfection. PHMB eye drops have been used as a treatment for eyes affected by Acanthamueba keratitis.

PHMB is also used as an ingredient in some contact lens cleaning products, cosmetics, personal deodorants and some veterinary products.

The PHMB hydrochloride salt (solution) is used in the majority of formulations.

An alternative biocide is Polyaminopropyl biguanide (PAPB), which is a disinfectant and a preservative used for disinfection on skin and in cleaning solutions for contact lenses. It is also an ingredient in many deodorant bodysprays. It is a polymer or oligomer where biguanide functional groups are connected by hexyl hydrocarbon chains, with varying chain lengths. PAPB is specifically bactericidal at very low concentrations (10 mg/l) and is also fungicidal.

The chemical structure of PAPB is shown below:

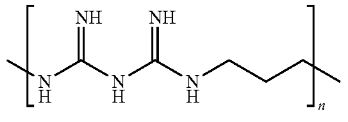

Petrolatum, also known as petroleum jelly, white petrolatum, soft paraffin or multi-hydrocarbon, (CAS number 8009-03-8), is a semi-solid mixture of hydrocarbons (with carbon numbers mainly higher than 25), and is commercially available from a variety of sources. Petrolatum has a melting point usually within a few degrees of human body temperature, approximately 37° C. (99° F.).

It is preferred that all components of the present stable suspension (water, petrolatum, and biocide) are USP and/or cosmetic grade or personal grade.

The biocide component of the present invention suspension is present in an amount of 0.1 to 10 wt %, based on total amount of the aqueous portion of the composition, preferably from 1 to 7.5 wt %, most preferably from 2 to 3 wt %. The petrolatum and aqueous phase are used in a ratio of from 50:1 to 10:1, preferably from 30:1 to 15:1, most preferably in a ratio of approximately 19:1.

The suspension of the present invention can be used to prepare ointments or other medicaments, useful in the treating of fungal, viral, and/or bacterial infections, and provide a time released biocide that does not wash away with exudate.

Optionally, the suspension of the present invention can contain one or more additional components that do not interfere with the biocidal activity or ionic charge of the vesicles. Such optional components include mineral oil (to lower the viscosity of the suspension), steroids (such as cortisone), or other medicaments to complement the biocidal nature of the suspension.

To prepare the stable suspension of the present invention, the petrolatum is preferably heated to a temperature just above its melting point, preferably at least 40° C., more preferably in the range of 45-50° C. The liquid biocide is preferably heated to the same or slightly higher temperature as the petrolatum, and the two combined. The mixture is then preferably stirred slowly until it becomes a semi-solid gel. This slow stirring can be performed manually or mechanically. At this point, the resulting semi-solid gel is subjected to a high speed, high torque mixing blade, at a mixing speed sufficient to disperse the liquid into nanovesicles smaller than 100 microns. Preferably, the mixing speed is greater than about 700 rpm. The resulting suspension remains stable, without coalescing, separating, or flocculating for extended periods of time.

In an alternative embodiment, the present invention suspension is prepared by heating the petrolatum to a point that it is half melted, then combined with the heated biocide/water combination, to generate a composition in semisolid state, which is then subjected to high shear mixing to generate the suspension as above.

The present invention biocidal suspensions permit the biocide to continue killing organisms over time without washing away or becoming depleted, and remaining in contact with the skin. The present invention suspension also allows drainage of the wound to occur to the outer dressing ideal for wound care.

In testing against various bacterial and viral strains, the present invention composition having PHMB at a concentration of 2.3 wt % (based on total aqueous phase), benzalkonium chloride at a concentration of 0.13 wt % (based on total aqueous phase), and a ratio of petrolatum to aqueous phase of approximately 19:1, and gave the following results:

| | *s. aureus* | *e. coli* | *p. aeruginosa* | *c. albicans* | *A. brasiliensis* | *s. aureus* (MRSA) | *E. faecalis* (VRE) | *K. pnuemoniae* (CRE) |
|---|---|---|---|---|---|---|---|---|
| Initial count (CFU/mL) | 445,000 | 467,500 | 530,000 | 450,000 | 240,000 | 152,500 | 322,500 | 465,000 |
| Initial Log | 5.6494 | 5.6698 | 5.7243 | 5.6532 | 5.3802 | 5.1833 | 5.5085 | 5.6675 |
| DAY 14 CFU/g recovered | <100 | <100 | <100 | <100 | 3.250 | <100 | <100 | <100 |
| log | 2.0000 | 2.0000 | 2.0000 | 2.0000 | 3.4983 | 2.0000 | 2.0000 | 2.0000 |
| log reduction from initial | 3.65 | 3.67 | 3.72 | 3.65 | 1.38 | 3.18 | 3.51 | 3.67 |
| DAY 28 CFU/g recovered | <100 | <100 | <100 | <100 | 2,850 | <100 | <100 | <100 |
| log | 2.0000 | 2.0000 | 2.0000 | 2.0000 | 3.4548 | 2.0000 | 2.0000 | 2.0000 |
| log reduction from initial | 3.65 | 3.67 | 3.72 | 3.65 | 1.93 | 3.18 | 3.51 | 3.67 |

This showed a nearly complete biocidal activity, even after 30 days.

Obviously, numerous modifications and variations of the present invention are possible in light of the above teachings. It is therefore to be understood that within the scope of the appended claims, the invention may be practiced otherwise than as specifically described herein.

What is claimed is:

1. A method of making a non-separating, non-coalescing, non-flocculating stable suspension comprising combining petrolatum at a temperature about 37° C. to about 45° C., with a liquid biocide to form nanovesicles of liquid biocide suspended in said petrolatum, said liquid biocide comprising a biocide and water mixture, said biocide comprising substantially all cationic molecules or all anionic molecules.

2. A method as in claim 1, wherein said petrolatum is at a temperature just above its melting point of approximately 37° C.

3. A method as in claim 1, wherein said petrolatum is at a temperature within the range of 37° C. to 40° C.

4. A method as in claim 1, wherein said petrolatum is at about 40° C.

5. The method of claim 1, wherein all ionic biocide compounds present are all cationic biocides.

6. The method of claim 1, wherein all ionic biocide compounds present are all anionic biocides.

7. The method of claim 1, wherein the at least one ionic biocide compound is selected from the group consisting of polyhexanide (PHMB), polyaminopropyl biguanide (PAPB), benzalkonium chloride, stearalkonium chloride, and sodium hypochlorite utilizing the salt forms where necessary to attain an ionic state.

8. The method of claim 7, wherein the at least one ionic biocide compound is a combination of PHMB and benzaikonium chloride, utilizing the salt forms where necessary to attain an ionic state.

9. The method of claim 1, wherein the suspension further comprises at least one nonionic biocide compound.

10. The method of claim 1, wherein the suspension further comprises at least one additional medicament.

11. The method of claim 10, wherein the at least one additional medicament is a steroid.

12. The method of claim 11, wherein the steroid is cortisone.

13. A non-separating, non-coalescing, non-flocculating stable suspension consisting of water, petrolatum and at least one cationic biocide; and optionally mineral oil, where the at least one cationic biocide is contained within nanovesicles having a diameter of 100 microns or less.

* * * * *